Figure 1:
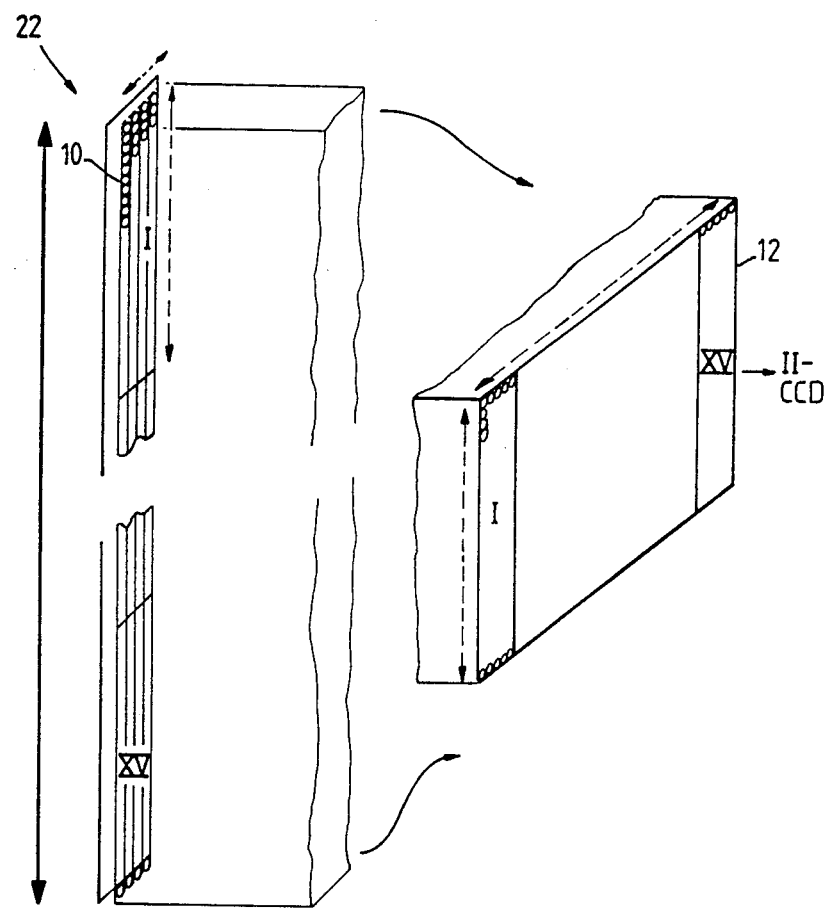

United States Patent [19]

Rushbrooke et al.

[11] Patent Number: 4,933,961

[45] Date of Patent: Jun. 12, 1990

[54] IMAGING SYSTEM

[75] Inventors: John G. Rushbrooke; Richard E. Ansorge, both of Cambridge, United Kingdom

[73] Assignee: British Aerospace Public Limited Company, London, England

[21] Appl. No.: 178,228

[22] Filed: Apr. 6, 1988

[30] Foreign Application Priority Data

Apr. 10, 1987 [GB] United Kingdom ............... 8708611
Jun. 1, 1987 [GB] United Kingdom ............... 8712773

[51] Int. Cl.$^5$ ..................... G01N 23/04; G01T 1/202
[52] U.S. Cl. ..................................... 378/57; 250/367; 250/368
[58] Field of Search ............... 378/146, 99, 57; 358/200; 250/227, 368, 213 VT, 367

[56] References Cited

U.S. PATENT DOCUMENTS

| | | | |
|---|---|---|---|
| 3,051,166 | 8/1962 | Hovnanian | 250/227 |
| 3,622,785 | 11/1971 | Irwin et al. | 250/213 VT |
| 3,652,855 | 3/1972 | McIntyre et al. | 250/227 |
| 3,790,785 | 2/1974 | Paolini et al. | 250/368 |
| 4,031,401 | 6/1977 | Jacob | 378/146 |
| 4,031,545 | 6/1977 | Stein et al. | 378/57 |
| 4,096,381 | 6/1978 | Brown | 250/213 VT |
| 4,142,101 | 2/1979 | Yin | 250/363 R |
| 4,160,165 | 7/1979 | McCombs et al. | 378/146 |
| 4,200,800 | 4/1980 | Swift | 378/10 |
| 4,228,357 | 10/1980 | Annis | 378/99 |
| 4,242,583 | 12/1980 | Annis | 378/146 |
| 4,242,588 | 12/1980 | Silk et al. | 378/34 |
| 4,245,158 | 1/1981 | Burstein et al. | 250/370.09 |
| 4,260,898 | 4/1981 | Annis | 378/146 |
| 4,342,914 | 4/1982 | Bjorkholm | 378/146 |
| 4,366,576 | 12/1982 | Annis | 378/146 |
| 4,389,729 | 6/1983 | Stein | 378/99 |
| 4,405,207 | 9/1983 | Kay | 350/320 |
| 4,414,682 | 11/1983 | Annis et al. | 378/146 |
| 4,415,810 | 9/1983 | Brown et al. | 250/367 |
| 4,472,822 | 9/1984 | Swift | 378/146 |
| 4,482,957 | 11/1984 | Bjorkholm | 358/111 |
| 4,503,332 | 3/1985 | Annis | 378/146 |
| 4,511,799 | 4/1985 | Bjorkholm | 250/367 |
| 4,593,355 | 6/1986 | Chase | 378/21 |
| 4,674,834 | 6/1987 | Margolin | 350/96.25 |
| 4,692,937 | 9/1987 | Sashin et al. | 378/146 |
| 4,721,851 | 1/1988 | Kogure | 250/227 |
| 4,736,102 | 5/1988 | Morrone | 250/484.1 B |

FOREIGN PATENT DOCUMENTS

| | | |
|---|---|---|
| 0046009A1 | 2/1982 | European Pat. Off. . |
| 0136732 | 7/1984 | European Pat. Off. . |
| 0131244A2 | 1/1985 | European Pat. Off. . |
| 3335621A | 4/1985 | Fed. Rep. of Germany . |
| 3346551A | 7/1985 | Fed. Rep. of Germany . |
| 1391042 | 4/1975 | United Kingdom . |
| 1539685 | 1/1979 | United Kingdom . |
| 2007457A | 5/1979 | United Kingdom . |
| 2076250A | 1/1981 | United Kingdom . |
| 2056671A | 3/1981 | United Kingdom . |
| 2085254A | 4/1982 | United Kingdom . |
| 2122837A | 1/1984 | United Kingdom . |
| 2137453A | 10/1984 | United Kingdom . |
| 2144960A | 3/1985 | United Kingdom . |
| 2167204A | 5/1986 | United Kingdom . |
| 2176680A | 12/1986 | United Kingdom . |

OTHER PUBLICATIONS

"X-Ray Detector for Non-Destructive Testing", Electronic Product Design, Jan. 1984, pp. 63–64.

Primary Examiner—Carolyn E. Fields
Attorney, Agent, or Firm—Nixon & Vanderhye

[57] ABSTRACT

An industrial x-ray inspection system has detecting means comprising a linear array of scintillator crystals operable to emit light in response to incident radiation, a bundle of optical fibers arranged so that an input end thereof is positioned at the detecting means for receiving light therefrom and an output end thereof is positioned at an image intensifier or camera wherein the optical fibers are regrouped so that the aspect ratios of the input and output ends of the bundle of optical fibers match those of the detecting means and the image intensifier or camera respectively. One optical fiber is associated with each scintillator crystal.

4 Claims, 2 Drawing Sheets

IMAGING SYSTEM

This invention concerns imaging systems and concerns particularly systems for imaging large objects. By large is meant objects having an area which is very much greater than the area of the radiation detector employed so that either only a very small part of the overall article can be seen by the detector at any instant or a very reduced scale (de-magnified) image of the article must be formed for viewing of the whole article by the detector.

Transportation of goods across frontiers in large containers presents a problem for security surveillance. Such containers, typically being of the order of 24 cubic meters in volume and weighing typically 20 tons are frequently used illicitly to import goods such as weapons, contraband, drugs and the like. X-rays of energy typically of the order of 5 to 10 MeV have sufficient penetration power to generate useful X-ray images of the interior of such containers and a particular embodiment of the present invention concerns an imaging system by which such containers can be subjected to X-ray surveillance.

In a system of the type proposed for investigating X-ray images for medical applications such as is described in UK Patent Specification No. 2176680A, the X-ray image is to be observed by means of a large area, thin fluorescent screen by an intensifying camera (such as a SIT vidicon or CCD camera).

A disadvantage of such large area fluorescent screen systems is that the X-ray image is downgraded in quality by scattered radiation, which can be typically several times as intense as the useful X-rays ie. those which have not undergone scattering in the container being surveyed.

European Patent Application No. 0233156 discloses an optical fibre scanning device for the formation of TV images in which a bundle of optical fibres is arranged linearly at one end and circularly at the other end. At the circular end there is an arrangement for scanning a single fibre so as to sample sequentially the outputs from the fibre bundle. This sequential sampling is inefficient as only the output from a single fibre in the bundle is being sampled at any one time.

It is an object of the present invention to provide an improved imaging system which can be used for viewing large objects.

According to the present invention we provide an imaging system comprising elongate detecting means operable to emit light in response to incident radiation, a bundle of optical fibres arranged so that an input end thereof is positioned at the detecting means for receiving light therefrom and an output end thereof is positioned at an image intensifier or camera wherein the optical fibres are regrouped so that the aspect ratios of the input and output ends of the bundle of optical fibres match those of the detecting means and the image intensifier or camera respectively.

An advantage of an imaging system of the invention is that the detector is a column or slit detector and is therefore much less susceptible to background scattered radiation than is a detector based on a wide angle fluorescent screen.

In practice a fibre bundle will deliver approximately 2% of the light from the detecting means to an image intensifier. On the other hand a lens viewing a similarly sized source of light will transmit typically less than 1 millionth of the light. Use of fibres thus allows both a reduction in the X-ray irradiation time and simultaneously a better spatial resolution. Typically an irradiation time of 8 milliseconds is possible with a spatial resolution of approximately 1.5 to 2 mm.

At any one time, the outputs from all of the optical fibres in the bundle is being utilised, ie. parallel processing is used, which is an efficient way of handling the incoming information.

Preferably, the output end of the bundle of optical fibres is positioned at the input of a demagnifying image intensifier. Also preferably the image intensifier is positioned adjacent to a CCD camera which may be of the dual zone type.

Where a CCD camera is employed, the pixel train (ie. the train of signals arising as the pixels are scanned) coming from the camera is most conveniently digitised using a flash analogue to digital converter (FADC).

Signal processing may be applied to the CCD output so as to reduce variation in noise level and sensitivity between one pixel source and another where more than one pixel is responsive to the light from 1 fibre, the signals for the pixels may be added so as to give a combined signal for the fibre concerned. Signal processing operations of this nature may be performed electronically using look up tables stored in RAM. Using such an approach, a digital representation of an article can be built up with a resolution corresponding to the fibre spacing and the resulting signals relating to the overall article may be stored in a digital frame store. Contributions to the overall image relating to any one point in the article will of course appear in each of the n columns (where an n column detector is employed) and will of course arise at different times and have to be appropriately combined. However, with a knowledge of the speed of the article relative to the detector and the spacing between the columns in the detector, this processing can be readily achieved.

In the embodiment to be described the detecting means emits light in response to X-radiation. Conveniently the contents of the store are displayed using a television monitor or the like to enable an operator to study a visual representation of the X-ray image of the article under surveillance.

The detecting means may comprise a screen material which fluoresces in response to X-radiation.

Alternatively the detecting means may comprise crystals which emit light in response to X-radiation.

The use of small crystals allows a higher resolution to be obtained than would be obtained from a slit detector of the same length and built from medium sized scintillating crystals. In addition, the cost including read out per channel of known crystal-silicon diode arrays is such that a system employing smaller crystals (of the order of $1 \times 1mm^2$ area) is likely to be more expensive than the crystal/fibre optic solution proposed by the present invention. Thus as compared with a crystal detector read out by silicon photodiodes, the invention allows better resolution except when viewing extremely impenetrable cargos equivalent for example to 25 cm of steel. For such cargos, adjacent image elements (corresponding to fibres) must be combined to avoid quantum mottle and in that event poorer resolution automatically will result. Preferably, if crystals are used, the spacing of the optical fibres is substantially equal to the spacing of the crystal centres.

In the embodiment to be described, the bundle of optical fibres comprises a plurality of columns of optical fibres. Thus, the column detector may include a certain degree of redundancy in that it is a plurality, say four, fibres wide in the direction of travel of the article and is therefore less vulnerable to crystal failure than where a single vertical column of crystals and associated fibres is employed.

In the embodiment to be described the imaging system comprises a plurality of bundles of optical fibres, each bundle having an associated detecting means and image intensifier or camera.

The imaging system may be adapted to image an article which is large relative to the width of the detecting means and which, in use, moves generally perpendicularly relative to the length of the detecting means. In one mode of satisfactory operation a steady container motion of 1.5 mm per 8 milliseconds is used. However, a significant variation in the actual container speed by 20% or so would lead to only a small loss of horizontal resolution. Nethertheless it may be necessary to limit vertical container vibration to speeds of this order (ie to a few millimetres per second) in order to preserve vertical resolution. However, the effect of large amplitude vertical vibration can be compensated for by monitoring the instantaneous vertical position of the container and deriving appropriate corrections.

These limitations are mentioned on the basis that a CCD camera with a clocking rate of 4 mHz is employed and a faster clocking rate for example 8 mHz would permit a corresponding increase of the speed of the article relative to the detector and in the case of a standard container would reduce the time for processing down to as little as 15 seconds.

Figure 2:
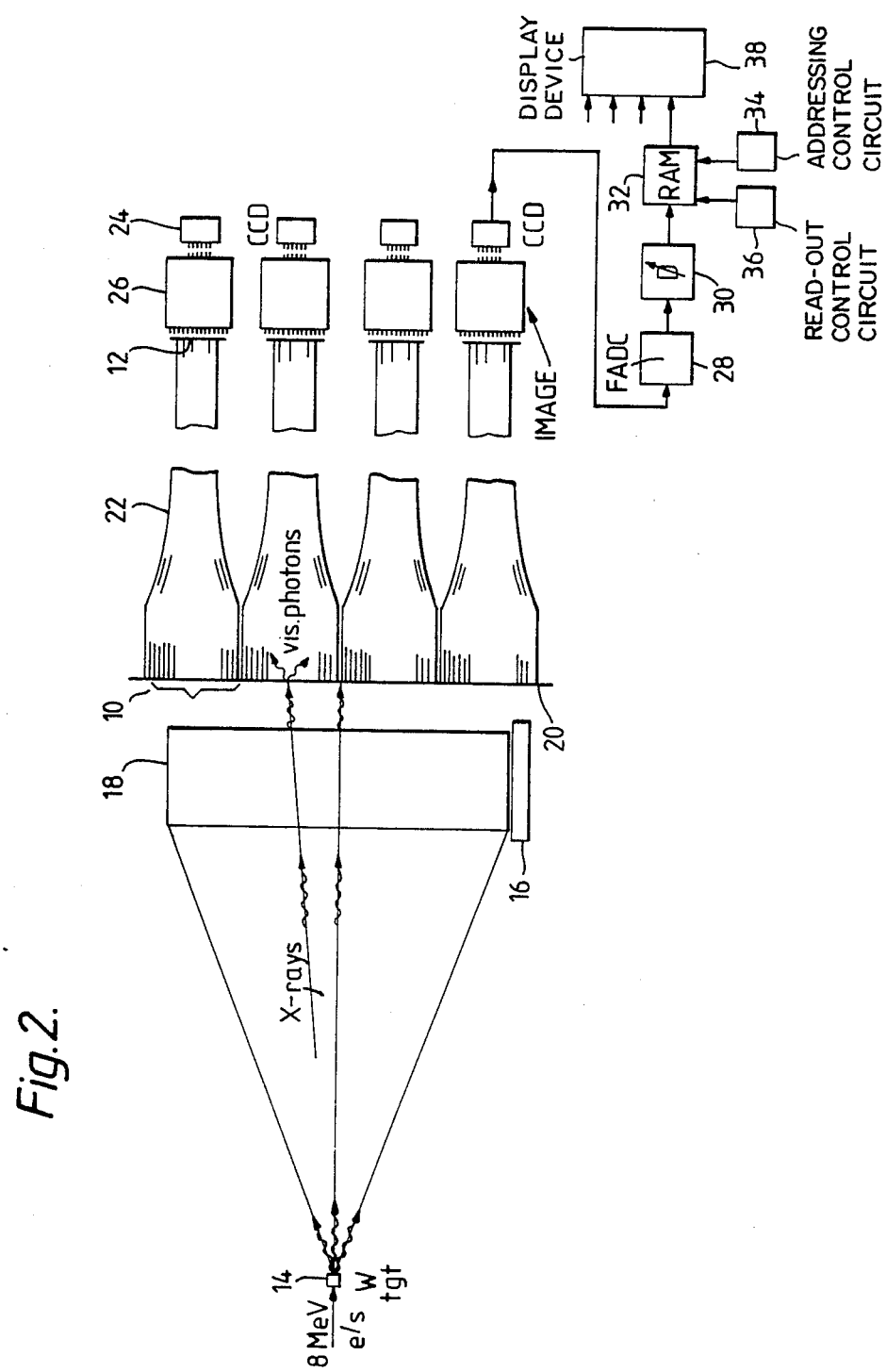

The invention will now be described, by way of example, with reference to the accompanying drawings, in which:

FIG. 1 illustrates how the aspect ratio of a fibre optic bundle forming part of an imaging system according to the present invention can be altered between the input end and the output end thereof, and FIG. 2 is an end view of an X-ray imaging system according to the invention.

FIG. 1 illustrates how a fibre optic bundle 22 consisting of four columns each containing 750 or so optical fibres and comprising an input end 10 in the shape of a strip can be rearranged at its output end 12 so as to present a regrouping of the fibres into an array of rows and columns having an aspect ratio which is very different from that of the input end 10. The output end 12 as shown has an aspect ratio of 1.2:1 but alternative aspect ratios of 3:2 or 4:3 may be provided by appropriate regrouping of the fibres.

It will be seen that the resulting aspect ratio of height to width at the input end 10 is very large and quite unlike the aspect ratio of any standard vidicon or CCD camera and is also unlike the aspect ratio of standard image intensifiers which are usually circular and typically have an input diameter of less than 100 mm. Whilst it is possible to envisage optically reducing the strip image or scanning the strip image mechanically by for example moving the image intensifier, all such arrangements introduce time delays and potential errors and risk a decrease in the signal to noise ratio of the system.

In accordance with the present invention the optical fibres are regrouped between the detector and the input to the image intensifier so as to alter the aspect ratio of the fibre optic array to use more completely the available area of the camera whether it be a CCD array or vidicon. The image intensifier output may be coupled to a CCD camera having a useful image area of width 5.8 mm by height 4.3 mm, made up of a matrix of 144 columns of pixels, each column containing 208 pixels. There are four fibre columns each 4500 mm high, containing 12,000 fibres in all viewing the strip image. One quarter vertical part of this arrangement of fibres comprising 3000 fibres could be rearranged into a matrix of 60 columns each having 50 fibres in each column so as to produce an aspect ratio somewhat closer to that of the imaging area of the CCD camera.

Numerous possibilities for regrouping exist because signal processing (described below) is used to re-constitute the true image from information about the geometrical positions of every fibre at both input and output.

Whilst the relative positions of the fibres as between input and output ends 10 and 12 are fixed, it is not necessary for the mapping of the fibres at the output end 12 to correspond to any particular pattern of the fibres at the input end 10, since the intention is that the output end 12 will be scanned using a high speed scanning camera or the like. The image at the output end 12 can be converted into electrical signals or digitised for storing in a random access memory. The mapping between the camera and the memory may be such as to insert appropriate electrical signals into the different store locations, so that a simple read out of the store will produce a reconstitution of the image from the input end 10. Alternatively the store locations may be read out in a particular pattern which is determined by the mapping between corresponding positions of the fibres from input to output, so that the image at the input end 10 is reconstituted by reading out the random access memory in the appropriate manner.

If a large enough memory and appropriate mapping both in a space and time domain are employed, it is possible to store within the random access memory a series of pictures each one corresponding to the optical image presented to the input end 10 from a succession of shots or exposures of an article which itself is larger than the input end 10 of the fibre optic bundle. Due to the relative movement an overall image is built up in the random access memory for subsequent read out using an appropriate addressing of the random access memory store locations.

In the envisaged arrangement, so as to accommodate the full height of the vertical image there are four columnar arrays such as the bundle 22 and each columnar array has an output end such as 12 for scanning by a separate CCD camera. The electrical signals from the various cameras must then be stored in an appropriate manner with further mapping between one camera output and another, so that the overall picture stored in the random access memory can be read out in an appropriate manner.

A fibre optic bundle 22 as shown in FIG. 1 and hitherto described is of particular application in the surveillance of large objects such as standard shipping retainers which are typically of the order of 6 meters long by 2 meters high and 2 meters wide. Such surveillance has become increasingly important to prevent smuggling particularly of weapons and the like and an embodiment of an imaging system according to the invention now to be described allows the interior of a sealed container to be inspected using an X-ray source.

FIG. 2 is an end view of an imaging system for inspecting containers of this nature and is positioned opposite an X-ray source 14 on one side of a path along which containers move on trailers, or a conveyer belt, or the like. A conveyer belt is designated 16 and positioned thereon is a container 18.

A preferred X-ray source is a LINAC or plurality of LINAC's operating typically at 8 MeV at a pulse frequency of 625Hz, so that exactly 5 pulses are delivered during each 8 millisecond period. A given point of the container will therefore receive 5.n pulses of X-radiation as it moves past n vertical fibre columns. If n is 4 as described above, there will be 20 pulses of X-radiation by the container as it moves past the four vertical columns of fibres. A LINAC capable of delivering an X-ray dose rate to the container of about 20 Rad per minute is therefore sufficient to produce useful images.

Typically a collimator is positioned between the container and the detector 20 so that the output from the LINAC or LINACS is collimated so as to irradiate uniformly the column detector.

Since the fibres will experience some of the irradiation, appropriate material should be chosen for the fibres and to this end preferably quartz fibres are Employed. Any fluorescent material or crystals used in the detector must also be radiation resistant.

The intention is to ensure that each point on the container 18 will receive 20 pulses of X-radiation as it moves past a vertical columnar detector 20 located on the other side of the container, remote from the X-ray source 14, the width of the detector 20 being such that any point on the container will take 32 milliseconds to pass from one side of the detector 20 to the other, as the container moves relative to the source 14. The detector 20 responds to incident X-radiation by exitting visible light and may, for example, comprise a material which fluoresces in response to X-radiation or may comprise an array of crystals which scintillate in response to X-radiation.

Where the detector comprises a continuous strip of fluorescent material, the latter may comprise $Gd_2O_2S$ in an emulsion, some 0.5 mm deep and 6 mm wide.

Where the detector is made up of a matrix of crystals, each typically has a $1 \times 1$ mm² face and is 5 mm deep.

Where fluorescent material or crystals having dimensions as indicated are employed, the core diameter of each optical fibre is typically 0.5 mm.

The spacing between the centres of the optical fibres determines the vertical resolution of the device and, where crystals are employed, the spacing between the crystal centres. Typically a spacing between fibre centres of 1.5 mm would be employed and this is a convenient spacing between the crystal centres. Whilst a single column of crystals or fluorescent material is theoretically all that is required, a plurality of separate columns, (or a matrix of crystals), are preferred so as to avoid the problem common to all strip detectors should one of the detectors fail (which results in a complete horizontal stripe missing from the final image). Typically the detector 20 will consist of four adjoining columns of crystals each column having an associated fibre column for viewing the crystals. Where fluorescent sheet material is employed, the material may be viewed by a number of fibre columns, the number being four for a 6 mm wide sheet read by fibres 1.5 mm apart, as considered above.

Where a standard container is to be viewed, the detector may be some 4500 mm high by 6 mm wide allowing four columns of 1 mm² crystals having a centre spacing of 1.5 mm, to be accommodated and viewed by a corresponding number of individual optical fibres.

X-rays which penetrate through the container 18, impinge on vertical detector 20 and the light given off by the detector 20 is coupled into the input end 10 of a fibre optic array generally designated 22 but only partially shown, the output of which is formed by regrouping the fibres in the manner described with reference to FIG. 1. The output end 12 of the fibre optic bundle 22 thereby has an aspect ratio more akin to that of a CCD camera or other scanning device, indicated by reference numeral 24 in FIG. 2, and the output window 12 couples to the input of a de-magnifying image intensifier 26 the output of which couples directly to a CCD camera 24.

Typically the individual fibres are regrouped at the input of the image intensifier 26 using a drilled aluminium spacer plate (not shown) in which the drilling are arranged to match the aspect ratio of the useful imaging area of the CCD camera 24. The spacer plate also determines and fixes the relationship between the original geometrical position of the fibres and the CCD pixels which eventually receive light therefrom.

Thus the four columns of fibres are viewed by four image intensifiers and each intensifier is arranged to view a quarter vertical part of the slit image. Thus, if there are 12,000 fibres and four image intensifiers, each image intensifier need only be concerned with 3000 fibres.

Some 10 pixels in the CCD array are linked to each one of the 3000 fibres in the arrangement for one read out. It will be seen that since only a quarter of the overall height of the slit image will be associated with each image intensifier, the distance between the remote ends of each quarter and the corresponding position of the fibres at the input of the image intensifier will be much less than if the remote ends of the single column were to be linked to each of four centrally located image intensifiers.

The electrical signals from the camera 24 are digitised using a flash ADC device 28 and 30. Processing is performed by electrical circuits whose function is to enhance signal to noise ratio, smooth out variation in sensitivity as between one area of the CCD array and another and generally enhance the digital signals derived from the ADC 28. The processed signals are stored in a random access memory 32, the storage addresses of which are selected during storage by a first control circuit 34.

If the imaging system is used in conjunction with standard shipping containers, the latter are typically arranged to move steadily passed the detector 20. If the CCD camera 24 is of the so called dual zone type having an image zone which accumulates an image over a period of 8 milliseconds and a read out zone which contains an earlier image whilst that is being clocked out (at typically 4 mHz) over the same 8 milliseconds, the read out zone can be updated at the end of each 8 millisecond period by shifting the accumulated charges in the image zone into the readout zone. Thus once an image read out is complete, the next image can be rapidly shifted (in a period of the order of 36 microseconds) into the read out zone. The container speed is arranged to be such that the distance moved by a point on the container during the 8 milliseconds period of image capture is equal to the fibre spacing. Thus it will be seen that where the fibre spacing is 1.5 mm and the image speed is 1.5 mm divided by 8 milliseconds, the maximum speed is 1.5 mm divided by 8 milliseconds, which is of the order of 0.19 m per second. The horizontal spatial resolution imposed by the fibre spacing is therefore not seriously degraded by the container motion and as indicated above will be the order of 2 mm.

From these considerations, it will be seen that a standard shipping container will need to move past the detector 20 at a speed of the order of 0.19 m/sec. giving a total scanning time of 30 seconds approximately per container.

In order to build up a complete picture of the X-ray image of the container 18, the light incident on the input end 10 of the fibre optic bundle 22 is converted into electrical signals as previously described using the CCD camera 24 and at the end of every 8 millisecond period electrical signals are digitised and stored in selected positions in the random access memory 32 under the control of circuit 34. After the whole of the length of the container has traversed the detector 20, the random access memory 32 will contain a large number of digital signals stored in groups of locations, each group corresponding to the light pattern incident on the detector 20 during one of the 8 millisecond exposures of the container. A picture of the entire container can then be obtained by suitably reading out the signals from the random access memory 32, typically under the control of a read out control circuit 36. The electrical signals can be used to create a visual display of the original container X-ray image using a television monitor or other type of display device 38.

In view of the regrouping of the optical fibres between the input ends 10 and the output ends 12 of the fibre optic bundles, the pattern of signals stored in the random access memory 32 at the end of each 8 millisecond exposure will of course not map directly to the pattern of light incident on the input end 10. However by appropriate decoding and reading out of the random access memory store locations in the appropriate manner, the electrical signals supplied to the display device 38 can be assembled and grouped in such a manner as to produce in the display a representation of the X-ray image of the container.

This display device receives signals from each of the four read outs corresponding to the four vertical parts of the image, and reconstitutes them into a physically correct image.

Since the information is static and stored in a semi-permanent basis, the display can be studied be an observer and different parts of the overall image inspected to any desired scale (limited only by the resolution of the system) in the event that closer inspection is required of any particular part of the X-ray image. This may for example be achieved by altering the mode of operation of the read out control system 36 so that only part of the random access memory is read out within the normal frame period of the display device 38, and the signals supplied thereto are suitably expanded in the horizontal and vertical sense so as to fully occupy the screen, thereby effectively magnifying that part of the original X-ray image.

Since any signal processing or the output of the random access memory 32 will be greatly simplified if the electrical signals stored therein map on a one to one basis with the corresponding points which would exist in the original X-ray image if the latter were to have existed on a single entity, the signal processing 30 and/or the input addressing control circuit 34 preferably operate in such a manner as to organise the storage of the digitised signals into memory locations within the memory 32 so that the positions of the digitised signals within the memory 32 are in the most convenient form for reading out and displaying in the display 38 and also are in a convenient form to allow for expansion and magnification of different parts of the stored picture.

The arrangement shown in FIG. 2 comprises four column windows each having an associated fibre optic bundle 22 of which a portion is shown leading to an output window 12. The four column windows correspond to the four vertical parts of the whole container image. The output from the fibre optic bundle associated with each such column window is regrouped and presented to a single image intensifier input window for feeding to a single CCD camera or the like.

As there are four vertical parts to the whole image there are four read outs, as shown in FIG. 2, each having its own image intensifier, and each coupling to its own CCD camera or other scanning device, with the signals from each of the cameras being processed separately in a corresponding plurality of circuit processing systems of the type shown in FIG. 2 for combination in one large random access memory or separate random access memories. The process of reconstitution of the overall picture entails reading out in strict sequence the appropriate sections of the large memory, of each of the random access memories, in turn, and presenting the signals in an appropriate train to a display device such as a television monitor.

It will be appreciated that the number of vertical columns of fibres can be different from four with an appropriate change in the number of image intensifiers and cameras.

It will be appreciated that where a single memory is to be employed, the multiplexing of the signals from the CCD cameras or other detectors such as 24 may take place before or after analogue to digital conversion so as to reduce the amount of circuitry which has to be duplicated.

The invention is of general application to the surveillance of large objects and is equally applicable to the inspection of containers of the type used in road, rail and shipping transport, as well as to the inspection of articles on conveyer belts in factories and the like.

Although mention has been made of movement of the article relative to the detector, it is of course to be understood that all such movement is entirely relative and where it is more appropriate, the article may be left stationary and the detector moved relative to the article, either in a horizontal or vertical or other direction so as to scan the article, whilst the latter remains stationary. This sort of arrangement, suitably scaled, would be appropriate to medical X-ray imaging, for example:

The source of X-rays may be moved with the detector or if more appropriate, the source may be arranged to flood the whole of one side of the article so that synchronous movement with the detector is not required.

Two or more such X-ray sources may of course be arranged and may be switched in sequence as the detector is moved, so as to cause different regions of the article to be flooded with X-rays as the detector moves relative to the article, in synchronism and appropriate sequence with the movement of the detector.

Although not envisaged is being particularly advantageous because it would require the use of excess detector means, it would be possible to provide a slit detector by placing a collimator in front of a wide area detector.

It is to be understood that the invention is not limited to the inspection of objects such as containers and in some situations the opticla fibre windows such as 10 may be arranged in patterns other than simple slits and may for example be arranged around part of the whole of a cylindrical surface so as to enable different scanning approaches to be adopted and differently shaped objects to be more conveniently inspected. Whatever the arrangement however, a regrouping of the fibres between the input and output ends of the fibre optic bundle between X-ray detection and image intensifier or camera, is employed, so as to convert the aspect ratio of the bundle to match more appropriately the aspect ratio of the image intensifier and/or the camera coupled thereto.

The term "light" when used herein is not to be construed as necessarily limited to visible electromagnetic radiation but maybe invisible such as infra-red or ultra violet radiation.

We claim:

1. An industrial X-ray inspection system for imaging the interior of an article, the system comprising:
   a high-energy X-ray source for producing X-rays for penetrating said article;
   a linear array of regularly spaced scintillator crystals, said array having a length, each crystal being elongate and being mounted with one end face facing said source for receiving X-rays from the source, and each crystal being operable to convert X-rays received thereby to light;
   support means for supporting said article between the source and the array and for producing relative movement between the article and the source and array in a direction transverse to the length of the array;
   image intensifier means comprising a two-dimensional area input plane and a two-dimensional area output plane and being operable for forming at said output plane an intensified image corresponding to an image received at said input plane;
   a plurality of optical fibers, one for each of said crystals and each fiber having one end supported adjacent the other end face of the respective crystal to receive light produced by that crystal, the other ends of the optical fibers being supported in a two dimensional plane array adjacent respective portions of the input plane of the image intensifier means; and
   television camera means coupled to the image intensifier means for receiving the image formed at the output image plane of the image intensifier means.

2. An industrial X-ray inspection system for imaging the interior of an article, the system comprising:
   a high-energy X-ray source for producing X-rays for penetrating said article;
   a linear array of regularly spaced scintillator crystals, said array having a length, each crystal being elongate and being mounted with one end face facing said source for receiving X-rays from the source, and each crystal being operable to convert X-rays received thereby to light;
   support means for supporting said article between the source and array and for producing relative movement between the article and the source and array in a direction transverse to the length of the array;
   image intensifier means, comprising a two-dimensional area input plane and a two-dimensional area output plane, for forming at said output plane an intensified image corresponding to an image received at said input plane;
   a plurality of optical fibers, one for each of said crystals and each fiber having one end supported adjacent the other end face of the respective crystal to receive light produced by that crystal, the other ends of the optical fibers being supported in a two-dimensional plane array adjacent respective portions of the input plane of the image intensifier means;
   television camera means coupled to the image intensifier means for receiving the image formed at the output image plane of the image intensifier means;
   analog to digital converter means, connected to the television camera means, for digitizing the image representative signal produced by the camera means; and
   digital signal processing means, connected to the converter means, for sorting the successive elements of the digitized image representative signal to correspond to the order of corresponding crystals in said linear array.

3. An industrial X-ray inspection system for imaging the interior of an article, the system comprising:
   a high-energy X-ray source for producing X-rays for penetrating said article;
   a linear array of regularly spaced scintillator crystals, said array having a length, each crystal being elongate and being mounted with one end and face facing said source for receiving X-rays from the source, and each crystal being operable to convert X-rays received thereby to light;
   support means for supporting said article between the source and the array and for producing relative movement between the article and the source and array in a direction transverse to the length of the array;
   a plurality of image intensifiers each comprising a two-dimensional area input plane and a two-dimensional area output plane and being operable for forming at said output plane an intensified image corresponding to an image received at said input plane;
   a plurality of groups of optical fibers, one fiber for each of said crystals and one group of fibers for each of said image intensifiers, the fibers of any one group each having one end supported in registration with the other end face of a respective one of a respective group of adjacent ones of the crystals for that fiber to receive the light produced by that crystal, and the other ends of the fibers of said one group being supported in a two-dimensional plane array adjacent the input plane of a respective image intensifier; and
   for each image intensifier, a television camera means, coupled to a respective image intensifier, for receiving the image formed at the output image plane of the respective image intensifier.

4. An industrial X-ray inspection system for imaging the interior of an article, the system comprising:
   a high-energy X-ray source for producing X-rays for penetrating said article;
   a plurality of side-by-side linear arrays of regularly spaced scintillator crystals, each array having a length, each crystal being elongate and being mounted with one end face facing said source for receiving X-rays from the source, and each crystal being operable to convert X-rays received thereby to light;

support means for supporting said article between the source and said arrays and for producing relative movement between the article and the source and arrays in a direction transverse to the lengths of the arrays;

a plurality of image intensifiers, each comprising a two-dimensional area input plane and a two-dimensional area output plane and being operable for forming at said output plane an intensified image corresponding to an image received at said input plane;

a plurality of groups of optical fibers, one fiber for each of said crystals and one group of fibers for each of said image intensifiers, the fibers of any one group each having one end supported in registration with the other end face of the respective one of a respective group of adjacent ones of the crystals for that fiber to receive light produced by that crystal, and the other ends of the fibers of said one group being supported in a two-dimensional plane array adjacent the input plane of a respective image intensifier; and for each image intensifier, a television camera means, coupled to the image intensifier means, for receiving the image formed at the output image plane of the image intensifier.

* * * * *